US00PP24018P2

(12) United States Plant Patent
Bourne

(10) Patent No.: US PP24,018 P2
(45) Date of Patent: Nov. 5, 2013

(54) ***DIANTHUS* PLANT NAMED 'WP10 XAV04'**

(50) Latin Name: *Dianthus×hybrida*
Varietal Denomination: WP10 XAV04

(76) Inventor: Carolyn Grace Bourne, Dawlish (GB)

( * ) Notice: Subject to any disclaimer, the term of this patent is extended or adjusted under 35 U.S.C. 154(b) by 37 days.

(21) Appl. No.: 13/134,818

(22) Filed: Jun. 15, 2011

Related U.S. Application Data

(60) Provisional application No. 61/398,930, filed on Jul. 2, 2010.

(51) Int. Cl.
*A01H 5/00* (2006.01)

(52) U.S. Cl.
USPC ..... Plt./281; Plt./272

(58) Field of Classification Search
USPC ..... Plt./272, 281
See application file for complete search history.

*Primary Examiner* — Susan McCormick Ewoldt

(57) ABSTRACT

A new cultivar of *Dianthus* plant named 'WP10 XAV04' which is characterized by a compact mounding habit, silver-gray foliage, fragrant fully double pink flowers with ruffled petal edges. In combination, these characteristics set 'WP10 XAV04' apart from all other existing varieties of *Dianthus* known to the inventor.

2 Drawing Sheets

Genus: *DIANTHUS*.
Species: ×*hybrida*.
Denomination: 'WP10 XAV04'.

BACKGROUND OF THE INVENTION

The present invention relates to a new and distinct cultivar of hardy garden pink or carnation that is grown for use as a flowering plant for pots and containers and for planting in the garden and landscape. The new cultivar is known botanically as *Dianthus×hybrida* and will be referred to hereinafter by the cultivar name 'WP10 XAV04'.

'WP10 XAV04' is a complex hybrid plant that is the product of a long term breeding program conducted by the inventor in a cultivated area of Houndspool, Dawlish, Devon, United Kingdom. The inventor selected 'WP10 XAV04' in 2004 for its fragrant pink fully double flowers, ruffled petal edges and silver-gray foliage.

'WP10 XAV04' resulted from the controlled cross pollination between two earlier selections of *Dianthus* from the inventor's breeding program, namely *Dianthus* 'Devon Flavia' (U.S. Plant Pat. No. 15,903) as female parent and Selection 'FLA 02.13' (unpatented and unreleased) as male parent.

'WP10 XAV04' is distinguishable from the female parent as follows: Whereas the flower of 'WP10 XAV04' is pink, fully double with ruffled petal edges, the flower of 'Devon Flavia' is lighter pink with a rose eye, semi-double with more fimbriated petals. In addition the foliage of the 'Devon Flavia' is blue-green in color, while the foliage of 'WP10 XAV04' is silver-gray in color.

'WP10 XAV04' is distinguishable from the male parent as follows: Whereas 'WP10 XAV04' has a compact mounding habit, the habit of the male parent is considerably taller and looser.

The variety of *Dianthus* which is considered by the inventor to most closely resemble 'WP10 XAV04' is the inventor's variety *Dianthus* 'WP08 NIK03' (U.S. Plant Pat. No. 21,418). The flowers of 'WP08 NIK03' are similar in size and shape but are magenta in color rather than the mid pink color of 'WP10 XAV04'. The foliage of 'WP08 NIK03' is gray-green in color, while the foliage of 'WP10 XAV04' is silver-gray. In addition, at nine months of age, the height of a plant of 'WP08 NIK03' is approximately half of the height of a plant of 'WP10 XAV04'.

Asexual reproduction of 'WP10 XAV04' was first accomplished by the inventor in 2004 in a cultivated area of Houndspool, United Kingdom. The method of asexual propagation used was vegetative cuttings. The inventor has determined that 'WP10 XAV04' is stable and reproduces true to type in successive generations of asexual propagation.

SUMMARY OF THE INVENTION

The following traits have been repeatedly observed and represent the characteristics of the new *Dianthus* cultivar 'WP10 XAV04'. These traits in combination distinguish this cultivar from all other commercial varieties known to the inventor. 'WP10 XAV04' has not been tested under all possible conditions and phenotypic differences may be observed with variations in environmental, climatic and cultural conditions, however, without any variance in genotype.

1. *Dianthus* 'WP10 XAV04' exhibits a compact mounding habit.
2. The flowers of *Dianthus* 'WP10 XAV04' are fully double.
3. The flowers of *Dianthus* 'WP10 XAV04' are pink in color.
4. The edges of the petals of *Dianthus* 'WP10 XAV04' are ruffled.
5. *Dianthus* 'WP10 XAV04' blooms from May through October.
6. *Dianthus* 'WP10 XAV04' exhibits silver-gray foliage.
7. At nine months of age, the height of the foliage mound of *Dianthus* 'WP10 XAV04' is 24 cm to 28 cm, and the width is 10 cm to 12 cm.
8. *Dianthus* 'WP10 XAV04' is perennial and is hardy at least to −15° C.
9. *Dianthus* 'WP10 XAV04' is suitable for use as a flowering plant in pots and containers.

BRIEF DESCRIPTION OF THE DRAWINGS

The accompanying color drawings illustrate the overall appearance of the new *Dianthus* variety 'WP10 XAV04' showing colors as true as it is reasonably possible to obtain in colored reproductions of this type. Colors in the drawings may differ from the color values cited in the detailed botanical description, which accurately describe the actual colors of the new variety 'WP10 XAV04'.

Figure 1:
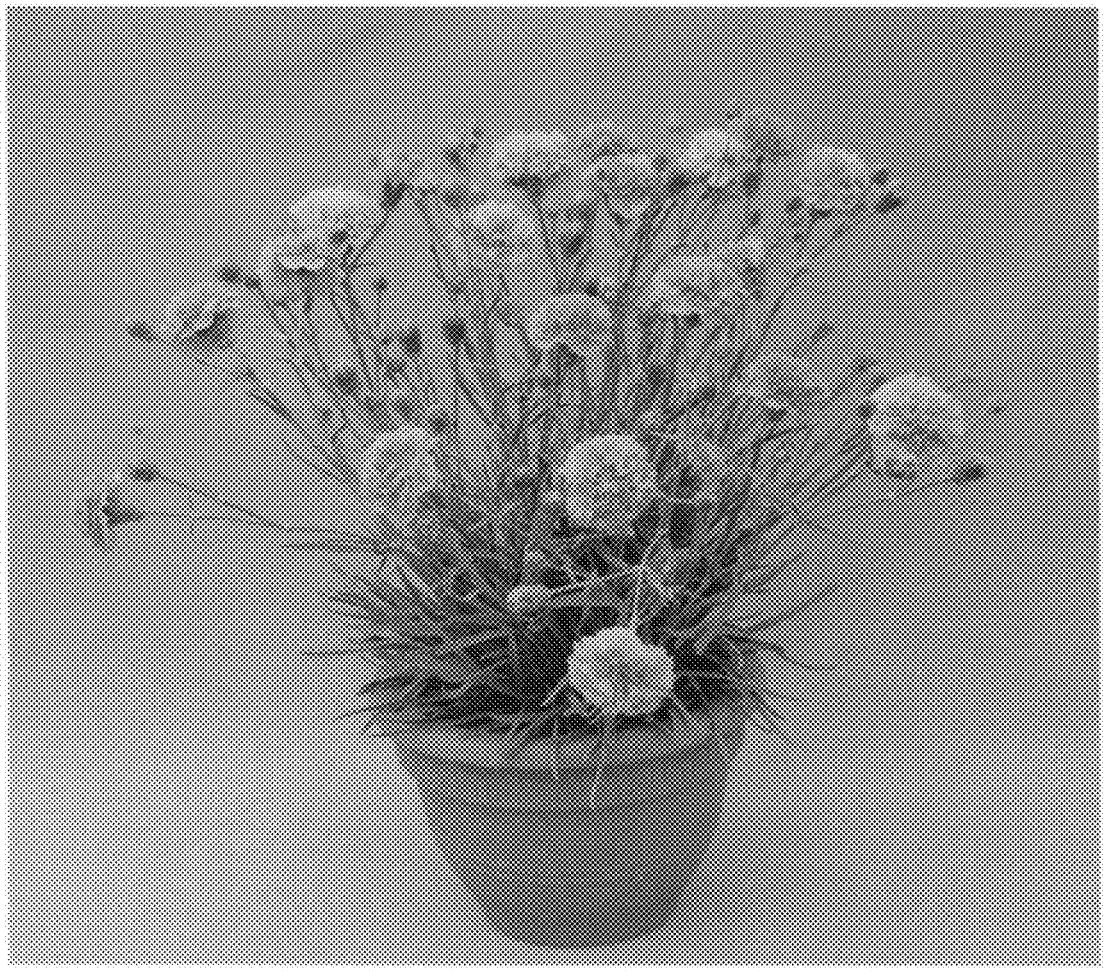

The drawing labeled as FIG. 1 depicts an entire flowering plant of 'WP10 XAV04'.

Figure 2:
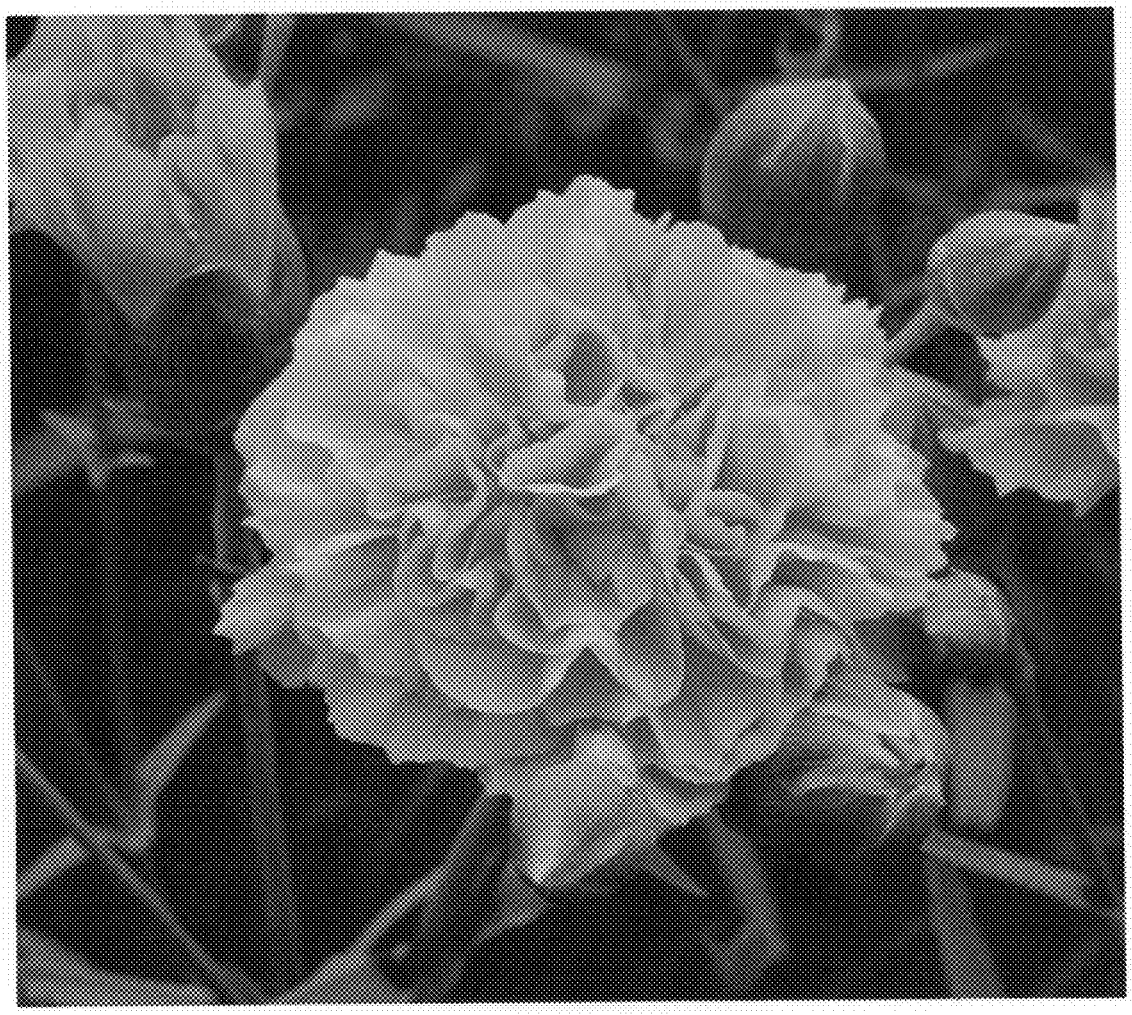

The drawing labeled as FIG. 2 depicts a close-up view of the flower of 'WP10 XAV04'.

All drawings were made from 9 months old plants which have been grown in 1.5-litre containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP10 XAV04'. Data was collected in spring from 1.5-litre container plants in spring, and grown indoors in a frost-protected greenhouse in Devon, United Kingdom. The color determinations are in accordance with the 2002 edition of The Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants.

Botanical classification:

Family: Caryophyllaceae.

Genus: *Dianthus*.

Species: ×*hybrida*.

Denomination: 'WP10 XAV4'.

Parentage: A complex *Dianthus* hybrid plant that resulted from the controlled cross pollination of the following parents.

Female parent: *Dianthus* 'Devon Flavia' (U.S. Plant Pat. No. 15,903).

Male parent: Unpatented selection of *Dianthus* from the inventor's breeding program, known as Selection 'FLA 02.13'.

Plant type: Flowering perennial.

Use of plant: As a flowering plant in containers, window boxes, planters, pots and the garden.

Bloom period: May-October in Devon, UK.

Plant habit: A compact mound with many branches and stems upright.

Height of plant: 24 cm to 28 cm after 9 months.

Width of plant: 10 cm to 12 cm after 9 months.

Hardiness: Has survived in temperatures of minus 15 Centigrade in Devon, United Kingdom. Early trials in the United States indicate survival in USDA Hardiness Zone 5.

Root system: Many fibrous roots.

Propagation method: Vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Temperature for rooting: A minimum of 15° C. air temperature and 21° C. base temperature at root level is required to produce roots on the cuttings.

Time to root cuttings: From 2 to 3 weeks is required to produce roots on a vegetative cutting using the rooting temperatures above.

Facilities for rooting: Mist propagation unit is required for satisfactory rooting of cuttings.

Crop time (from planting a rooted cutting): From 3-4 months (Spring planting) to 6-9 months (Fall planting).

Plant stem:

*Shape*.—Cylindrical.

*Height*.—15 cm to 17 cm.

*Diameter*.—2 mm.

*Surface*.—Glabrous and glaucous.

*Color*.—188A.

*Branching*.—Numerous shoots from the axils of the lower leaves.

*Internode length*.—20 mm-55 mm between nodes.

*Node dimensions*.—6 mm in diameter and 4 mm in length.

Leaf:

*Type*.—Evergreen.

*Shape*.—Linear, straight.

*Division*.—Simple.

*Apex*.—Acute

*Base*.—Decurrent.

*Venation*.—Not prominent.

*Margins*.—Entire.

*Arrangement*.—Opposite and spiraling on stem.

*Attachment*.—Sheathing.

*Surface* (*adaxial and abaxial*).—Glaucous.

*Stipules*.—Absent.

*Fragrance*.—Absent.

*Dimensions*.—Length: 7.5 cm to 8.5 cm. Width: 4 mm.

*Color*.—Adaxial surface: N189C. Abaxial surface: N189C.

Inflorescence:

*Flower stem*.—Length: 15 cm-17 cm. Width: 2 mm. Stem strength: Erect. Stem color: 188A.

*Inflorescence*.—Cymose.

*Type*.—Salviform, symmetrical.

*Development*.—Singly, in sequence from the uppermost bud.

Buds:

*Shape*.—Globular.

*Dimensions*.—18 mm in length and 11 mm in width.

*Color*.—Ranges between N138B and N138C on apical half and 143C on basal half.

*Surface texture*.—Glabrous.

Flowers:

*Number*.—3 to 5 per stem.

*Pedicel dimensions*.—15 cm-17 cm length and 2 mm in width.

*Pedicel strength*.—Erect.

*Pedicel color*.—188A.

*Flower dimensions*.—Length (including calyx): 36 mm. Diameter: 48 mm.

*Flower shape*.—Circular.

Flower profile: Reflexed.

*Lastingness*.—10 days at 20° C., on the plant.

*Fragrance*.—Moderate to strong, floral.

*Flowering period*.—May to October, in Devon, United Kingdom.

Corolla:

*Shape* (*upper part of corolla*).—Convex.

*Shape* (*lower part of corolla*).—Concave.

*Petal arrangement*.—Persistent, apopetalous, overlapping.
*Petal margin*.—Crenate-dentate, appears ruffled.
*Indentation*.—Varies between 0 mm and 1 mm.
*Petal texture*.—Soft.
*Flower type*.—Double.
*Petal number*.—Ranges from 35 to 40.
*Petal dimension*.—Length: 35 mm. Width: 24 mm.
*Color of upper surface*.—Ground color of blade: 62A. Color of band across blade: No band. Color of middle of strap: Ranges between 145C and 145D. Color of base of strap: Ranges between 145C and 145D.
*Color of lower surface*.—Ground color of blade: Ranges between 62B and 62C. Color of middle of strap: Ranges between 145C and 145D. Color of base of strap: Ranges between 145C and 145D.
*Petal shape*.—Obdeltoid.
*Petal apex*.—Fan shaped.
*Petal base*.—Strap shaped, tapering towards base.
*Petal surface*.—Glabrous.

Calyx:
*Shape*.—Cylindrical, diameter 14 mm.
*Sepals*.—Number: 5. Apex: Subacute. Base: Fused: sepals become free at 5-8 mm below the apex. Longitudinal profile: Flat-convex. Dimensions: Length: 22 mm. Width: 6 mm. Color, both surfaces: Ranges between 137B and 137C fading to 137D at base. Anthocyanin: Absent. Splitting: Not observed.

Epicalyx:
*Bracts number*.—1 pair of two.
*Shape of outer lobe*.—Acuminate.
*Dimensions*.—Width: 7 mm. Length: 9 mm.
*Color*.—Ranges from 133B and 133C.
*Anthocyanin*.—Absent.

Bracteoles:
*Number*.—1 pair of 2.
*Dimensions*.—Width: 12 mm. Length: 10 mm.
*Color*.—Ranges from 133B and 133C.
*Anthocyanin*.—Absent.

Reproductive organs:
*Stamens*.—Number: 10-15. Filaments: Color: White. Dimensions: 20-30 mm in length and 0.5 mm in width. Anthers: Number: 0 to 15. Color: 161D. Length: 1 mm; diameter: 0.5 mm. Attachment: Dorsifixed.
*Pollen*.—Present occasionally.
*Pollen color*.—11D.
*Style*.—Number: 2 to 3. Shoulder: Absent. Color: White. Length: 20 mm. Width: 1 mm.
*Stigma*.—Number: Single. Color: White to very light pink. Dimensions: 5 mm above petals at maturity.
*Ovary*.—Position: Superior. Dimensions: Length: 9 mm; diameter: 5 mm. Shape: Spindle. Color (upper surface): Ranges between 143C and 145B. Color (lower surface): 145C.
*Seed*.—Seed has not been found during repeated observations.

The invention claimed is:

1. A new and distinct cultivar of *Dianthus* plant named 'WP10 XAV04' as described and illustrated herein.

* * * * *